US008532768B2

(12) United States Patent
Doerr

(10) Patent No.: US 8,532,768 B2
(45) Date of Patent: Sep. 10, 2013

(54) ELECTROTHERAPY DEVICE FOR TREATING TACHYCARDIAC ARRHYTHMIAS OF A HEART

(75) Inventor: Thomas Doerr, Berlin (DE)

(73) Assignee: BIOTRONIK CRM Patent AG (CH)

(*) Notice: Subject to any disclaimer, the term of this patent is extended or adjusted under 35 U.S.C. 154(b) by 530 days.

(21) Appl. No.: 12/480,093

(22) Filed: Jun. 8, 2009

(65) Prior Publication Data

US 2009/0306729 A1    Dec. 10, 2009

(30) Foreign Application Priority Data

Jun. 10, 2008 (DE) .......................... 10 2008 002 331

(51) Int. Cl.
*A61N 1/36* (2006.01)
(52) U.S. Cl.
USPC ................................. 607/14; 607/4
(58) Field of Classification Search
USPC ........................................ 607/4, 14
See application file for complete search history.

(56) References Cited

U.S. PATENT DOCUMENTS

| 5,063,928 A * | 11/1991 | Grevis et al. ...................... 607/14 |
| 5,843,134 A | 12/1998 | Thong et al. |
| 5,999,854 A * | 12/1999 | Deno et al. ....................... 607/18 |
| 6,400,986 B1 * | 6/2002 | Sun et al. ......................... 607/14 |
| 6,801,806 B2 * | 10/2004 | Sun et al. ......................... 607/14 |
| 7,353,060 B2 * | 4/2008 | Sun et al. ........................... 607/5 |
| 7,522,956 B2 * | 4/2009 | Krig et al. .......................... 607/4 |
| 7,536,224 B2 * | 5/2009 | Ritscher et al. ................... 607/14 |
| 7,653,431 B2 * | 1/2010 | Cazares et al. ................. 600/515 |
| 7,818,056 B2 * | 10/2010 | Kim et al. ........................... 607/5 |
| 2002/0058968 A1 | 5/2002 | Sun et al. |
| 2004/0111121 A1 | 6/2004 | Brown et al. |
| 2004/0167579 A1 * | 8/2004 | Sharma et al. .................. 607/14 |
| 2005/0070966 A1 | 3/2005 | Sharma |
| 2005/0090869 A1 | 4/2005 | Sun et al. |
| 2006/0052829 A1 * | 3/2006 | Sun et al. .......................... 607/4 |
| 2007/0049974 A1 | 3/2007 | Li et al. |

FOREIGN PATENT DOCUMENTS

WO    WO 01/76688 A    10/2001

OTHER PUBLICATIONS

European Search Report, EP 09 15 9868, Aug. 26, 2009.

* cited by examiner

*Primary Examiner* — Joseph Stoklosa
(74) *Attorney, Agent, or Firm* — Craig A. Fieschko, Esq.; DeWitt Ross & Stevens S.C.

(57) ABSTRACT

An electrotherapy system, particularly an implantable heart stimulator, is configured as an electronic implant for electrical anti-tachycardia therapy of the heart, and includes at least one programmable therapy sequence (i.e. a sequence of several therapies that are delivered, one after the other, to treat a VT/VF episode). The implant has a therapy success memory for storing therapy success statistics for each therapy, as well as a therapy control unit that is configured to automatically undertake adaptation of the order of the therapies within a therapy sequence as a function of currently stored therapy success statistics.

18 Claims, 9 Drawing Sheets

| Energy: | (25J) | (30J) | 40J | 40J | 40J | 40J | 40J | 40J |
|---|---|---|---|---|---|---|---|---|
| Polarity: | normal | normal | normal | inverse | normal | invers | normal | inverse |
| Puls shape: | Biphase | Biphase | Biphase | Biphase | Biph.2 | Biph.2 | Biph.2 | Biph.2 |

FIG. 9

ELECTROTHERAPY DEVICE FOR TREATING TACHYCARDIAC ARRHYTHMIAS OF A HEART

FIELD OF THE INVENTION

The invention relates to an electrotherapy device for treating tachycardiac arrhythmias of a heart by use of electrical stimulation pulses or electrical defibrillation shocks.

BACKGROUND OF THE INVENTION

Electrotherapy devices for treating tachycardiac arrhythmias are known in the art, for example in the form of implantable cardioverters/defibrillators (ICDs). The devices serve to detect tachycardiac arrhythmias, such as atrial flutter or atrial fibrillation, and to end them, if possible, by means of targeted delivery of a therapy sequence that contains at least one electrostimulation pulse or defibrillation shock. In this respect, the ventricular tachycardiac arrhythmias, such as atrial flutter (ventricular tachycardia) or atrial fibrillation (ventricular fibrillation), are of particular interest. These ventricular tachycardiac arrhythmias can have their origin in the ventricle itself, and are referred to as ventricular tachycardia (VT) in the narrower sense or as ventricular fibrillation (VF). If the ventricular tachycardiac arrhythmia of the ventricle has its origin in the related atrium of the heart or in the sinus node, the ventricular tachycardiac arrhythmias are referred to as supraventricular tachycardia (SVT).

In the case of ventricular fibrillation, uncoordinated contraction of the ventricle in question occurs due to circulatory excitation of the myocardium (heart muscle tissue), leading to the result that the ventricle is no longer able to transport blood. However, some amount of coordinated contraction can still be found in the case of atrial flutter. Atrial fibrillation and atrial flutter are differentiated, for example, in that the frequency of the excitation is still greater in the case of atrial fibrillation than in the case of atrial flutter. Methods of detecting and differentiating the different tachycardiac arrhythmias are known in the art.

Also known are various therapy sequences for terminating a tachycardiac arrhythmia. These include anti-tachycardia stimulation (anti tachycardia pacing or ATP) in the form of an overdrive stimulation, in which stimulation pulses are delivered at a stimulation rate that is elevated as compared with the intrinsic (tachycardiac) heart rate that is present; and delivery of cardioversion shocks or delivery of defibrillation shocks, where the former usually have a lower energy than the latter. Defibrillation shocks are supposed to make the entire myocardium of an affected heart chamber refractory at the same time, and thus temporarily unresponsive to excitation, in order to thereby interrupt a circulating excitation of the heart muscle in question. Other therapy sequences, such as anti-tachycardia stimulation (ATP), include multiple, more energy-rich stimulation pulses for cardioversion of the heart chamber in question. The therapy sequences therefore differ in the number of stimulation pulses or defibrillation shocks delivered, for example, and in the point in time at which individual stimulation pulses or defibrillation shocks are delivered, i.e., at which a stimulation pulse follows a prior stimulation pulse for cardioversion.

If a cardioversion of a ventricular tachycardia (VT/atrial flutter) is supposed to take place in the form of overdrive stimulation as a therapy sequence, stimulation pulses are delivered which have an overdrive stimulation rate that is elevated as compared with the intrinsic (tachycardiac) heart rate. This is intended to interrupt a reentry cycle of excitation of the myocardium, which is typical for ventricular tachycardias (VT/atrial flutter), by means of a stimulation pulse that takes place before the natural (intrinsic) excitation of the heart chamber in question.

From the art, implantable cardioverters/defibrillators (ICDs) are known which are configured to first detect a tachycardiac arrhythmia, and to deliver therapy sequences of different ranking for treating a tachycardiac heart arrhythmia that has been detected. In this respect, first a therapy sequence having a low rank is delivered, which usually includes delivering stimulation pulses having low energy, which are thus more easily tolerated by the patient. If a low-ranking therapy sequence does not lead to successful termination of the tachycardiac heart arrhythmia, a therapy sequence having a higher ranking is triggered. Usually, the therapy sequence having the highest ranking is the (painful) delivery of a defibrillation shock. Furthermore, ICDs are known that are configured to detect ventricular tachycardias and assign them to one of several VT zones. For example, a VT zone may include ventricular tachycardias within a particular heart rate range. The detection of a ventricular tachycardia in a specific VT zone causes these known ICDs to first trigger the therapy sequence that last led to successful termination of the ventricular tachycardia in this VT zone. If this therapy sequence does not lead to therapy success (i.e. does not terminate the ventricular tachycardia), a different therapy sequence is subsequently triggered. If this becomes necessary, the other therapy sequence is used as the first therapy sequence when the next tachycardiac heart arrhythmia in this VT zone is detected.

US 2007/0049974 deals with systems for selecting therapy sequences having different rankings on the basis of a morphology analysis of the electrocardiogram that characterizes the tachycardiac heart arrhythmia.

The known mechanisms for adapting the therapy sequence are therefore restricted to an increase in the shock energy (i.e. the transition from a therapy sequence that is lower in rank to one that is higher in rank) as a reaction to a tachycardiac heart arrhythmia, in the event that the current therapy sequence proves to be unsuccessful; or to one-time delivery of a therapy sequence that previously proved to be successful; or to weakening of a therapy sequence that was repeatedly unsuccessful.

SUMMARY OF THE INVENTION

The invention attempts to present an anti-tachycardia heart stimulator that optimizes therapy sequences for treating tachycardia, between two aftercare intervals, as independently as possible with regard to therapy efficiency.

The invention is exemplified by an electrotherapy system, particularly an implantable heart stimulator, which is configured as an electronic implant for electrical anti-tachycardia therapy of the heart by means of at least one programmable therapy sequence (i.e. a sequence of multiple therapies that are delivered, one after the other, to treat a VT/VF episode). A therapy success memory stores therapy success statistics for each therapy, and a therapy control unit is configured to automatically adapt the order of the therapies within a therapy sequence as a function of currently stored therapy success statistics.

The therapy success statistics are preferably implemented in the form of therapy success counters for an anti-tachycardia therapy. The associated therapy success counter readings are stored in the therapy success memory. Anytime that the therapy success registration unit detects a therapy success after an anti-tachycardia therapy that has just been delivered, i.e. an end of the treated tachycardia, for example, the therapy success counter reading for this therapy is incremented (e.g., increased by 1).

For different types of tachycardias (slow, fast, or fibrillation, and with a stable or unstable rhythm in each instance), separate therapy success counters can be provided. Preferably, the control unit of the therapy system is then configured in such a manner that after detection and categorization of a tachycardia, it first triggers that anti-tachycardia therapy from a therapy sequence that has the highest counter reading for the tachycardia detected.

To review in greater detail, components of a preferred therapy system include:
- at least one stimulation unit that is connected or can be connected, using an electrode line, with an intracardiac stimulation or defibrillation electrode, and which is configured to generate and deliver electrical stimulation pulses and/or electrical defibrillation shocks,
- a (therapy) control unit that is connected with the stimulation unit, and is configured to control the stimulation unit to deliver different anti-tachycardia therapies, in accordance with therapy sequences stored in memory. Each anti-tachycardia therapy includes at least the delivery of a stimulation or defibrillation pulse. Different anti-tachycardia therapies differ in at least one therapy characteristic, such as the intensity of the stimulation pulse or defibrillation pulse, the number of pulses, or the order and points in time of individual pulses,
- a tachycardia registration unit that is connected or can be connected with an intracardiac detection electrode, by way of an electrode line, and is configured to record an intracardiac electrocardiogram signal and to process it in such a manner that the tachycardia registration unit can detect a tachycardia of an atrium or of a chamber of a heart, and record characteristics that characterize a tachycardia,
- a therapy success registration unit that is connected with a therapy success memory, and is configured to register an end of a tachycardiac arrhythmia (after delivery of a therapy sequence) as a therapy success, and to store data in the therapy success memory. The data characterize the tachycardiac arrhythmia as well as the anti-tachycardia therapy within a therapy sequence, that led to successful termination of the tachycardiac arrhythmias, and to compile therapy success statistics on the basis of the data stored in the therapy success memory,
- where the control unit is connected with the therapy success memory and configured, on the basis of the therapy success statistics stored in the therapy success memory, to determine the order of anti-tachycardia therapies of a future therapy sequence to be used after detection of a tachycardiac arrhythmia. The order of the anti-tachycardia therapies within the therapy sequence depends on how frequently an anti-tachycardia therapy led to successful termination of a tachycardia, in comparison with other anti-tachycardia therapies of the therapy sequence.

The therapy registration unit can be an integral part of the control unit, and may cause the control unit to trigger an anti-tachycardia therapy from a corresponding therapy sequence, if applicable.

As mentioned previously, the therapy success registration unit, in combination with the therapy success memory, may be configured as a therapy success counter, to increase a stored counter reading with regard to an anti-tachycardia therapy, if this anti-tachycardia therapy was successful. The counter readings of the therapy success counters then form the therapy success statistics.

Preferably, the tachycardia registration unit is configured to differentiate stable and unstable tachycardias—i.e. tachycardias that are accompanied by a stable or unstable (irregular) heart rhythm—from one another. Further, the therapy success registration unit, in combination with the therapy success memory as a therapy success counter, is configured to increase one of two counter readings assigned to an anti-tachycardia therapy, one of which is assigned to unstable tachycardias, and the other to stable tachycardias, depending on whether a tachycardia that has already been successfully terminated was classified as stable or as unstable by the tachycardia registration unit. In other words, two therapy success counters are provided for an anti-tachycardia therapy, namely one that is raised after any successful anti-tachycardia therapy of a tachycardia having an unstable rhythm, and one that is raised after any successful anti-tachycardia therapy of a tachycardia having a stable rhythm. In this manner, the therapy sequences for different types of tachycardias can be specifically optimized.

Separate therapy success counters may also be provided for differently "fast" tachycardias, for example, for slow tachycardias that are accompanied by a heart rate that falls into a predetermined range of heart rates (referred to as "VT1 zone"); for fast tachycardias that fall into a "VT2 zone" that is assigned to a range of higher heart rates than the "VT1 zone"; and ventricular fibrillations (VF) which fall into a range of very high heart rates (referred to as the "VF zone").

For this purpose, the tachycardia registration unit is preferably configured to assign a recorded tachycardia to one of at least two tachycardia zones, in such a manner that the assignment to one of the tachycardia zones clearly takes place as a function of a tachycardiac heart rate. Depending on the assignment of a detected tachycardia, the control unit is configured to use one of at least two therapy sequences, each of which is assigned to a tachycardia zone.

Furthermore, the tachycardia registration unit is preferably configured to record a tachycardia that accelerates after an anti-tachycardia therapy has been delivered.

In connection with this, the control unit can be configured to count the related therapy success counter down by 1 or to set its counter reading to "0" after detection of an accelerating tachycardia as the result of delivery of an anti-tachycardia therapy, in order to thereby bring about the result that the anti-tachycardia therapy in the therapy sequence is delivered with a lower ranking (at most).

As an alternative, the therapy success counter can be configured to store a blocking identifier for an anti-tachycardia therapy, and the therapy success registration unit can be configured to assign the blocking identifier to an anti-tachycardia therapy in the therapy success memories if this anti-tachycardia therapy led to an accelerating tachycardia. The control unit is then configured to completely remove an anti-tachycardia therapy that has been marked with a blocking identifier from any newly formed therapy sequence. Thus, the anti-tachycardia therapy marked with a blocking identifier is no longer delivered for treatment of a tachycardia that has been accelerated as the result of the anti-tachycardia therapy. The blocking identifier is therefore therapy-specific and tachycardia-specific.

Preferably, separate therapy success counters are further provided for the fundamental therapy type of anti-tachycardia stimulation (ATP) and shock delivery. The fundamental types of anti-tachycardia therapy can, in turn, represent a number of individual therapies. For example, different forms of shock delivery can be differentiated according to energy, pulse shape (e.g. monophase, biphase) and polarity, and can be assigned to a separate therapy success counter as different anti-tachycardia therapies.

Thus, there are the following versions of the therapy success counter, which can be used individually or in varying combinations:

(a) The therapy success counter readings are recorded separately for ATP and shock.
(b) The therapy success counter readings are recorded separately for each individual therapy.
(c) The therapy success counter readings are recorded separately for each individual therapy, and separately for stable and unstable tachycardias.
(d) The therapy success counter readings for shocks are recorded separately for each shock energy.
(e) The therapy success counter readings for shocks are recorded separately for each shock polarity.
(f) The therapy success counter readings for shocks are recorded separately for each shock pulse shape.

Also, combinations of the configurations according to (c) to (e) are possible.

With regard to the handling of the counter readings, as well as the optimization of the therapy sequence, the following versions can be used individually or in combination:

An acceleration of the rhythm, triggered by an anti-tachycardia therapy, causes the control unit to delete or reduce the success quota of the therapy in the therapy success statistics.

An acceleration of the rhythm, triggered by the therapy, causes the control unit to block the ATP therapy in the therapy success statistics.

The statistics used for therapy sequence optimization can be queried during aftercare by a physician, by means of an external programming device (programmer).

The therapy success counter readings in the therapy success memory can be deleted by the physician, individually or as a whole, by means of the programmer.

The therapy success counter readings in the therapy success memory can be automatically adapted (deleted or corrected) during reprogramming of the therapy sequence.

Therapy sequence optimization by means of the control unit can be turned on and off by the physician, by means of a programmable parameter.

According to a particularly preferred version of the invention, the electrotherapy device is configured as follows:

Two therapy success counters are stored in memory for each ATP attack and each shock in the VT zones—therapy success in the case of stable VT, and therapy success in the case of unstable VT.

The ventricular stability criterion immediately before the detection or redetection is always used for the stability assessment.

A therapy success counter is stored in memory for each shock in the VF zone.

The therapy success counter is incremented if the therapy leads to termination detection.

The therapy success counter is decremented if the therapy is followed by redetection in the same or a lower zone.

The therapy success counter is deleted if the therapy is followed by redetection in a higher zone (acceleration).

The therapy success counter remains unchanged if the therapy (DFc) or the episode (programmer) was discontinued.

The therapy success counters are only influenced by spontaneous episodes, i.e. not in the case of induced episodes.

The therapy success counters can be queried by the programmer during aftercare.

The therapy success counters can be manually reset, using the programmer.

The therapy success counters are automatically reset by the programmer during reprogramming of the therapy sequences, ATP, and shock parameters.

If a shock having an energy less than maximal energy is followed by redetection, then an "energy increase" flag is set in the therapy success counter; in this case, the therapy success counter is not decremented.

If "Prefer ATP" is turned off, then ATPs that lead to acceleration are blocked (spec. code in the therapy success counter).

If Automatic Therapy Optimization is turned on, then the order of the therapy sequence is resorted in accordance with the counter reading of the therapy success counters.

First, the programmed number of ATP attempts is delivered, but not in the programmed order, and rather in the order of decreasing therapy success, separated according to stable and unstable VT at the time of detection/redetection.

If all the ATP attempts have been delivered without success, then the number of programmed shocks is delivered in the order of decreasing therapy success. If the energy increase of a shock is marked, the shock energy of this shock is set to maximal energy.

Other preferred versions of the invention result from the combinations of the characteristics described above, but are not explicitly discussed here.

BRIEF DESCRIPTION OF THE DRAWINGS

The invention will now be explained in greater detail, using an exemplary version, and making reference to the figures. The figures show:

FIG. 9: an exemplary overview of various therapy parameters for a defibrillation shock.

DETAILED DESCRIPTION OF PREFERRED VERSIONS OF THE INVENTION

Figure 1:
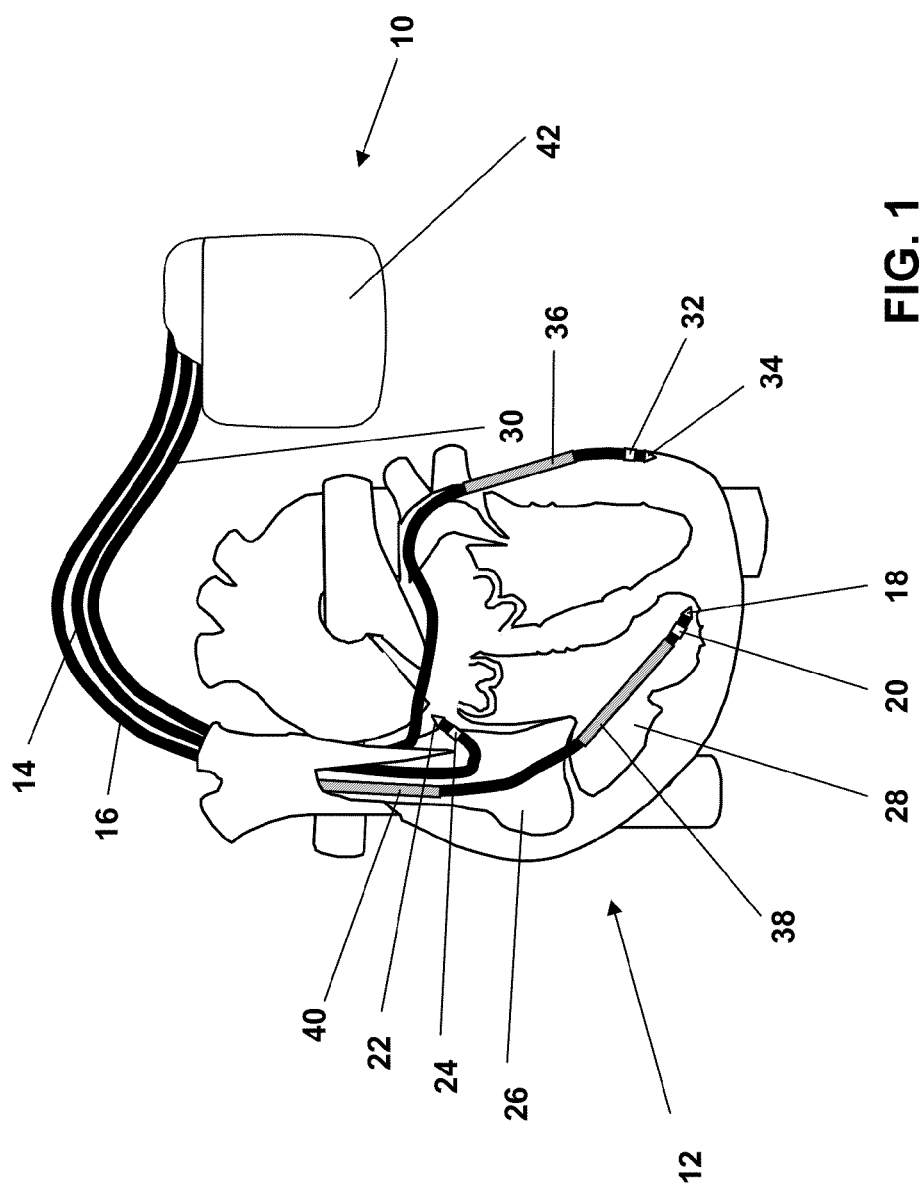
FIG. 1: an implantable three-chamber cardioverter/defibrillator as an example of a heart stimulator, with associated connections to electrode lines.

FIG. 1 shows an implant 10 in the form of a biventricular three-chamber heart pacemaker and cardioverter/defibrillator (ICD). Three electrode lines are connected to it, namely a right-atrial electrode line 14, a right-ventricular electrode line 16, and a left-ventricular electrode line 30. In the implanted state, the right-atrial electrode line 14 ends in the right atrium 26 of a heart 12. The right-ventricular electrode line 16 ends in the right ventricle 28 of the heart 12, and the left-ventricular electrode line 30 reaches all the way to the left ventricle of the heart, by way of the coronary sinus of the heart 12.

The right-atrial electrode line 14 carries a right-atrial tip electrode (RA Tip) 22 at its distal end, and, at a slight distance from that, a right-atrial ring electrode (RA Ring) 24. In similar manner, the right-ventricular electrode line 16 carries a right-ventricular tip electrode (RV Tip) 18 at its distal end, and, at a slight distance from that, a right-ventricular ring electrode (RV Ring) 20. A left-ventricular tip electrode (LV Tip) 34, and, at a slight distance from that, a left-ventricular ring electrode (LV Ring) 32, are also affixed to the distal end of the left-ventricular electrode line 30. These electrodes serve to record electrical potentials in the heart chamber, and to deliver stimulation pulses to the heart chamber, during normal pacemaker operation.

The right-ventricular electrode line 16 furthermore carries a right-ventricular shock coil (RV Coil) 38 as a defibrillation electrode, which is disposed in the right ventricle in the implanted state, as well as a second shock coil (SVC Coil) 40 situated in the superior vena cava in the implanted state. A left-ventricular shock coil (LV Coil) 36 is also affixed to the left-ventricular electrode line 30. The shock coils serve as defibrillation electrodes, if needed, to deliver defibrillation shocks.

Figure 2:
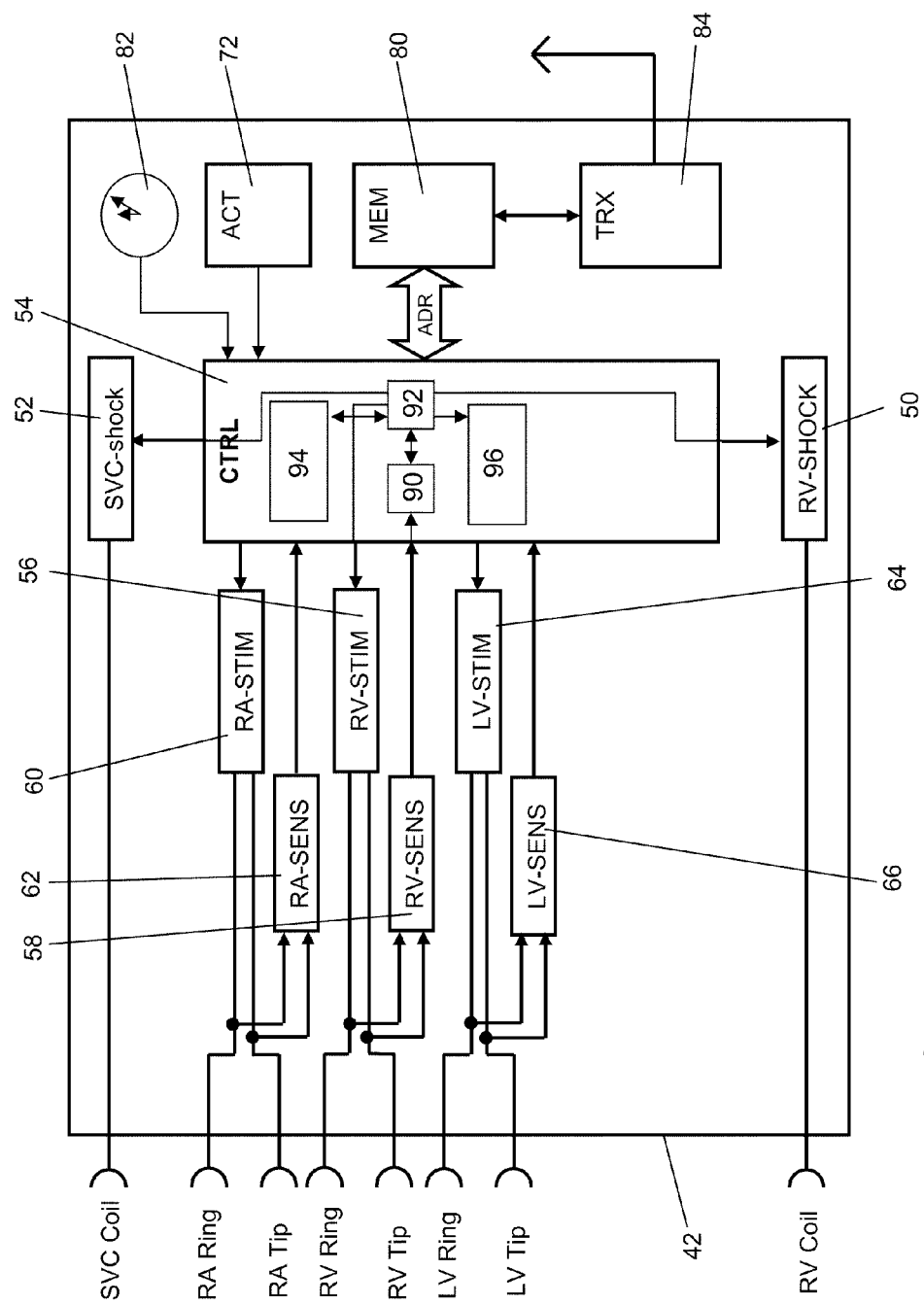
FIG. 2: a schematic block diagram of the heart stimulator from FIG. 1.

FIG. 2 shows the main components of the heart stimulator 10. On the left side, the electrical connections for the various electrodes 18, 20, 24, 22, 26, 32, 34, 38, and 40 are shown. The shock electrodes RV Coil 38 and SVC Coil 40 are respectively connected with a right-ventricular shock pulse generator 50 and SVC shock generator 52. The two shock generators 50 and 52 are connected with a stimulation control unit 54 that controls the two shock pulse generators 50 and 52 to generate and deliver a defibrillation shock, as necessary. If necessary, the shock electrode LV Coil 36 can also be connected with a shock generator (not shown in FIG. 2), which is also controlled by the stimulation control unit 54.

The connection for the right-ventricular tip electrode RV Tip 18 as well as the connection for the right-ventricular ring electrode RV Ring 20 are both connected with a right-ventricular stimulation unit 56 and with a right-ventricular sensing unit 58. Both the right-ventricular stimulation unit 56 and the right-ventricular sensing unit 58 are connected with the stimulation control unit 54.

The right-ventricular stimulation unit 56 is configured to generate a right-ventricular stimulation pulse in response to a control signal of the stimulation control unit 54, and to deliver it at the connector for the right-ventricular ring electrode RV Ring 20 and the right-ventricular tip electrode RV Tip 18. Alternatively, the housing 42 of the heart stimulator 10 may form a neutral electrode, and the right-ventricular stimulation unit 56 may be connected with the connector for the right-ventricular tip electrode RV Tip 18 and with the housing 42 as the other electrode for delivery of a stimulation pulse. A right-ventricular stimulation pulse differs from a defibrillation shock in that the stimulation pulse possesses a significantly lesser pulse intensity, so that it does not suddenly excite the complete heart tissue (myocardium) of a heart chamber, like a defibrillation shock does, and rather only excites the heart muscle cells in the immediate vicinity of the right-ventricular tip electrode RV Tip 18. This excitation then spreads further over the entire right ventricle 28, by means of natural stimulus conduction, and thus provides for stimulated contraction of the right ventricle 28.

The right-ventricular sensing unit 58 is configured to first reinforce the electrical potentials that are applied at the connector for the right-ventricular ring electrode RV Ring and the right-ventricular tip electrode RV Tip, by means of an input amplifier, and to filter them. Furthermore, the right-ventricular sensing unit 58 is configured to analyze the progression of the electrical signals that are applied to its inputs in such a manner that the right-ventricular sensing unit 58 independently detects a natural (intrinsic), i.e. independent, contraction of the right ventricle 28. This can be done, for example, in that the progression of the signal applied to the inputs of the right-ventricular sensing unit 58 is compared with a threshold value. Typically, the greatest amplitude of the signal—called the R wave—is characteristic of a natural contraction of the right ventricle 28, and can be detected by means of a threshold value comparison. The right-ventricular sensing unit 58 then issues a corresponding output signal, indicating a natural contraction of the right ventricle 28, to the stimulation control unit 54.

In an analogous manner, the connector for the right-atrial tip electrode (RA Tip) 22 and the connector for the right-atrial ring electrode (RA Ring) 24 are connected both with a right-atrial stimulation unit 60 and also with a right-atrial sensing unit 62, which in turn are connected with the stimulation control unit 54. The right-atrial stimulation unit 60 is configured to generate stimulation pulses whose intensity is sufficient to excite the right-atrial myocardium. In this connection, the right-atrial stimulation pulses can possess a different pulse intensity than the right-ventricular stimulation pulses. The right-atrial sensing unit 62 is configured to detect what is called a P wave from the progression of the difference signal applied at its inputs, which wave characterizes a natural (intrinsic) contraction of the right atrium 26. If the right-atrial sensing unit 62 detects a corresponding P wave, it generates an output signal and passes this on to the stimulation control unit 54, which signal characterizes a natural contraction of the right atrium 26.

In the same manner, the connector for the left-ventricular tip electrode LV Tip 54 and the connector for the left-ventricular ring electrode LV Ring 32 are also connected with a left-ventricular stimulation unit 64 and a left-ventricular sensing unit 66. The left-ventricular stimulation unit 64 and the left-ventricular sensing unit 66 are also connected with the stimulation control unit 54. The two function in similar manner as the stimulation units 56 and 60 and sensing units 58 and 62 described above.

As another component of the heart stimulator 10, an activity sensor 72 is connected with the stimulation control unit 54 and integrated into the housing 42 of the heart stimulator 10. The activity sensor 72 is configured to register a movement signal that depends on the physical activity of a patient, and to issue a corresponding first signal to the stimulation control unit 54 to indicate the physical activity of the patient. This allows the stimulation control unit 54 to adapt the timing of the stimulation pulses to the hemodynamic needs of the patient.

Furthermore, the heart stimulator 10 includes a memory unit 80 that is connected with the stimulation control unit 54, and which allows signals generated or analyzed by the stimulation control unit 54 to be stored in memory. The memory unit 80 also makes it possible to store control programs for the stimulation control unit 54 in memory, preferably in changeable form. Furthermore, the stimulation control unit 64 is connected with a timer 82.

The memory unit 80 is connected with a telemetry unit 84 that makes it possible to transmit data stored in the memory unit 80 to an external programming device (programmer, not shown) in a wireless manner, or to transmit programming commands from the external programming device 100 to the heart stimulator 10 and to store them in the memory unit 80.

The control unit 54 is configured to trigger and control different therapy sequences for treating tachycardiac arrhythmias. For this purpose, the control unit is particularly configured to classify ventricular tachycardias that have been detected in one of three tachycardia zones, depending on how high is the detected ventricular heart rate (ventricular frequency): ventricular tachycardia having a low ventricle frequency, VT1; ventricular tachycardia having a higher ventricle frequency, VT2; and ventricular fibrillation, VF.

The control unit 54 preferably possesses different subunits. This includes a tachycardia registration unit 90 configured to detect and classify a tachycardia on the basis of the sensing events delivered by the right-ventricular sensing unit 58, namely a tachycardia of the VT zone 1, the VT zone 2, or the VF zone, depending on the heart rate. In addition, an actual therapy control unit 92 is configured to turn on the right-ventricular and/or the left-ventricular shock generator 52 and/or 54, or the right ventricular stimulation unit 56, after a tachycardia has been registered by the tachycardia registration unit 90. These steps treat a detected ventricular tachycardia, either by delivery of an anti-tachycardia stimulation (ATP) by way of the right-ventricular stimulation unit 56, or by delivery of a defibrillation shock by way of the right-ventricular shock coil 38 or the shock coil 40 in the superior vena cava. In combination with the tachycardia registration unit 90, the therapy control unit 92 also defines a therapy success registration unit which determines, after delivery of an anti-tachycardia therapy (i.e., after an anti-tachycardia stimulation or a defibrillation shock), whether or not the treatment of the tachycardia was successful. Such determination is made by analyzing the ventricular heart rate (using the sensing events delivered by the right sensing unit 58), determining if tachycardia is no longer present, or whether the treatment of the tachycardia was not successful and the tachycardia continues to exist. Furthermore, the therapy control unit 92, in combination with the tachycardia registration unit 90, is configured to also detect an accelerating tachycardia that results from delivery of an anti-tachycardia stimulation or delivery of a defibrillation shock, if applicable.

Which anti-tachycardia therapy the therapy control unit 92 delivers as a reaction to a detected tachycardia—i.e., which type of anti-tachycardia stimulation or which type of defibrillation shock is delivered—depends, at least in part, on the type of tachycardia detected. As an example, the delivered therapy may depend on the zone into which the tachycardia falls; whether the tachycardia is stable or unstable; and on a therapy sequence stored in the therapy sequence memory 94. In this respect, a separate therapy sequence is preferably assigned to every type of tachycardia, in other words a therapy sequence for a tachycardia of the VT zone 1, a therapy sequence for a tachycardia of the VT zone 2, and a therapy sequence for a ventricular fibrillation (VF zone). A therapy sequence contains different anti-tachycardia therapies in a stored order. The different anti-tachycardia therapies can be differentiated, once again, by whether they involve anti-tachycardia stimulation (ATP) or defibrillation shocks. In turn, the anti-tachycardia stimulations can be differentiated by the energy of the stimulation pulses and the point in time of delivery of the stimulation pulses. The defibrillation shocks can also be differentiated by shock energy, shock polarity, and pulse shape (monophase or biphase, for example). Accordingly, there are multiple different anti-tachycardia stimulations and multiple different defibrillation shocks within a therapy sequence.

For continuous optimization of the therapy sequence by the therapy control unit 92, a therapy success memory 96 is provided, and contains therapy success statistics. These therapy success statistics are formed by different counter readings, where each counter reading is assigned to an anti-tachycardia therapy, and to a tachycardia to be treated, as will be explained in greater detail below. The therapy control unit 92 is configured to increase or decrease the individual counter readings of the therapy success statistics in the therapy success memory 96, depending on whether a delivered anti-tachycardia therapy led to therapy success, or did not lead to therapy success, or actually lead to an acceleration of the tachycardia to be treated. Furthermore, the therapy control unit 92 is configured to rearrange the therapy sequences stored in the therapy sequence memory 94 on the basis of the therapy success counter readings in the therapy success memory 96, in such a manner that the anti-tachycardia therapy whose therapy success counter reading is the highest, and which therefore promises the best prospects of success for treating the specifically detected tachycardia, is delivered first within a tachycardia sequence.

Figure 3:
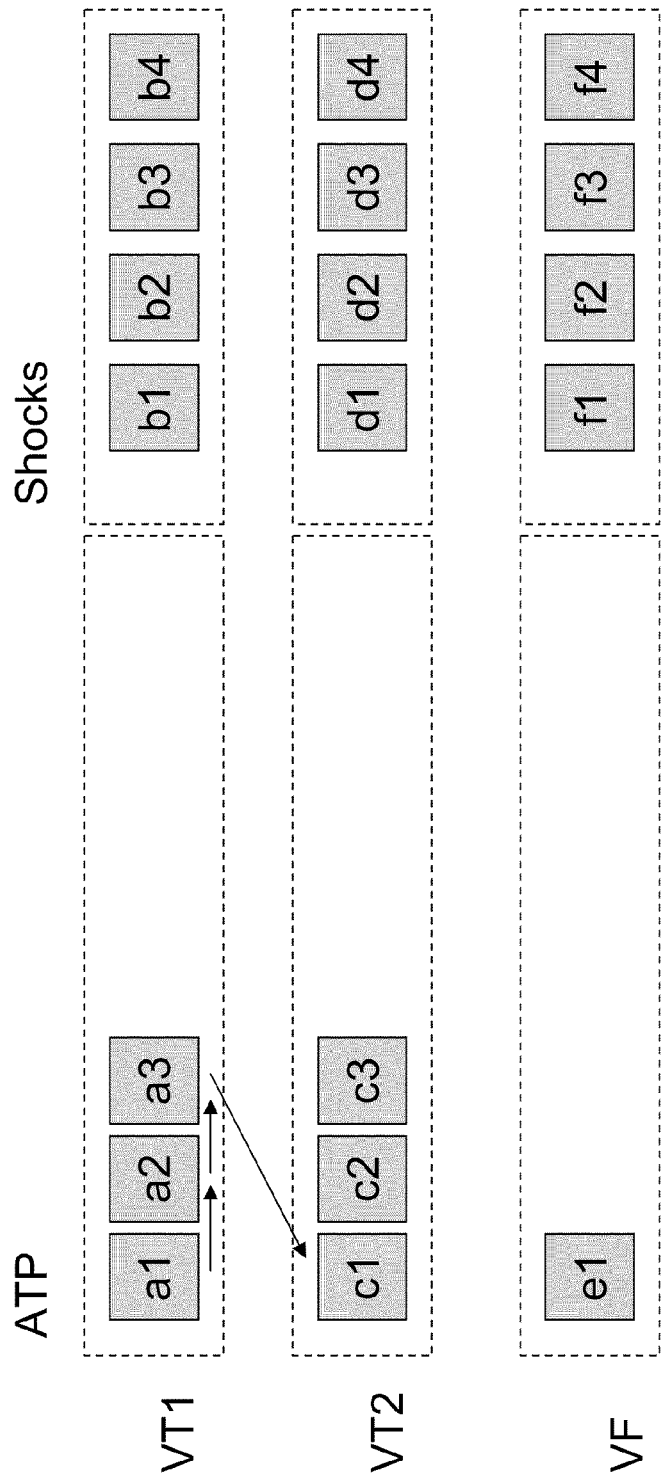
FIG. 3: a therapy sequence structure as it is available in current ICD systems.

FIG. 3 shows a therapy sequence structure as provided in current ICD systems. Each zone (VT1, VT2, VF) has a number of anti-tachycardia therapy attempts assigned to it. First, ATP therapies are defined, and then multiple defibrillation shocks. These therapy attempts can be individually configured with the programming device, by means of parameters such as (for example) the number of stimulation pulses and the stimulation interval for ATP, shock energy, shock polarity, or shock pulse shape.

If an initial detection takes place in one of the VT/VF zones, then the therapy sequence is delivered in the same order every time, from left to right, until either therapy success (detection of termination) has been recorded, or all the therapies of the therapy sequence have been used up.

Figure 4:
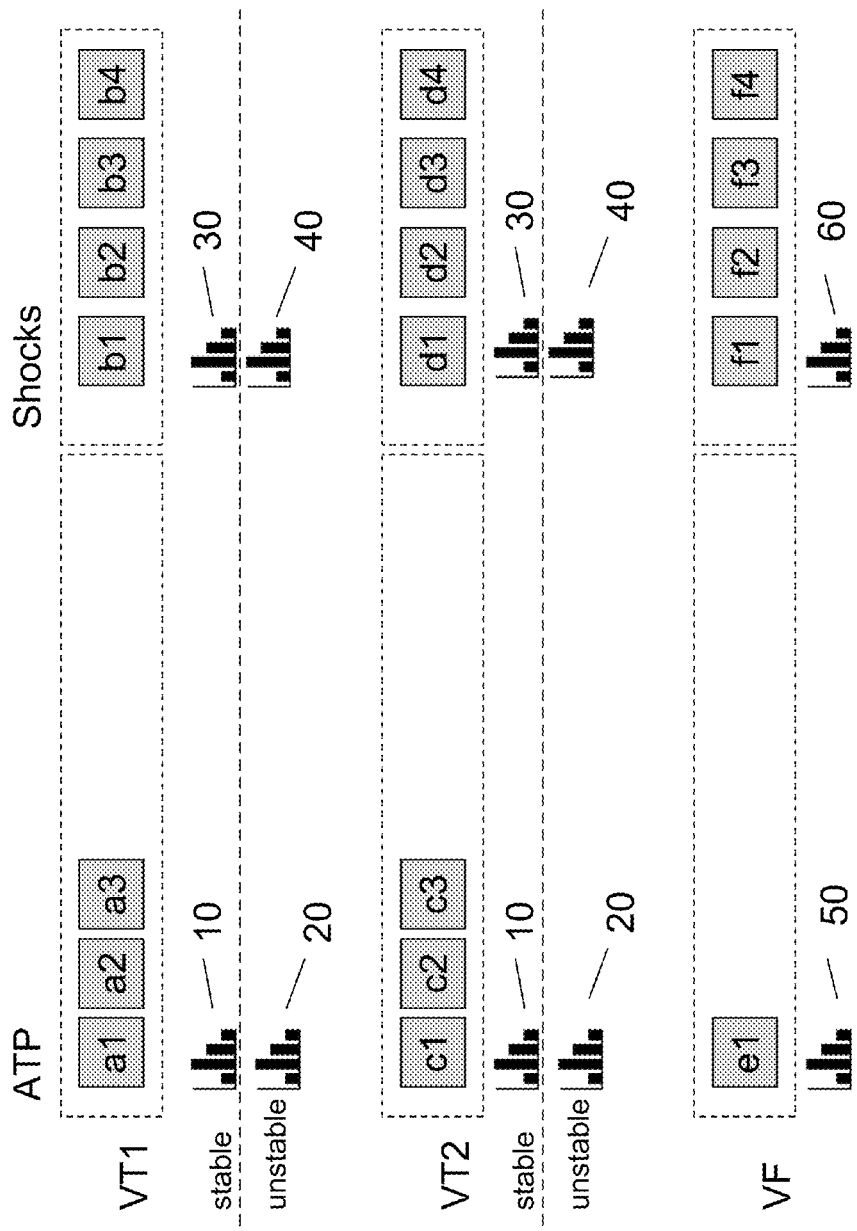
FIG. 4: the structure of a therapy success memory.

FIG. 4 shows the expanded therapy sequence structure according to the invention. Here, an additional memory region in the electronic implant is used to carry out a therapy success count for the therapies in each of the individual zones. The therapy successes of the individual ATP attempts in the VT1 zone for stable VT (10) and unstable VT (20) are counted. The therapy successes of the individual shocks in the VT1 zone, also distinguished by stable VT (30) and unstable VT (40), are counted.

As with the VT1 zone, therapy success counters for the ATP attempts and shocks, separated by stable and unstable VT, are provided in the VT2 zone.

In the VF zone, separation by stable and unstable arrhythmia is eliminated, and thus therapy success counters for ATP (50) and shocks (60) are provided.

Figure 5:
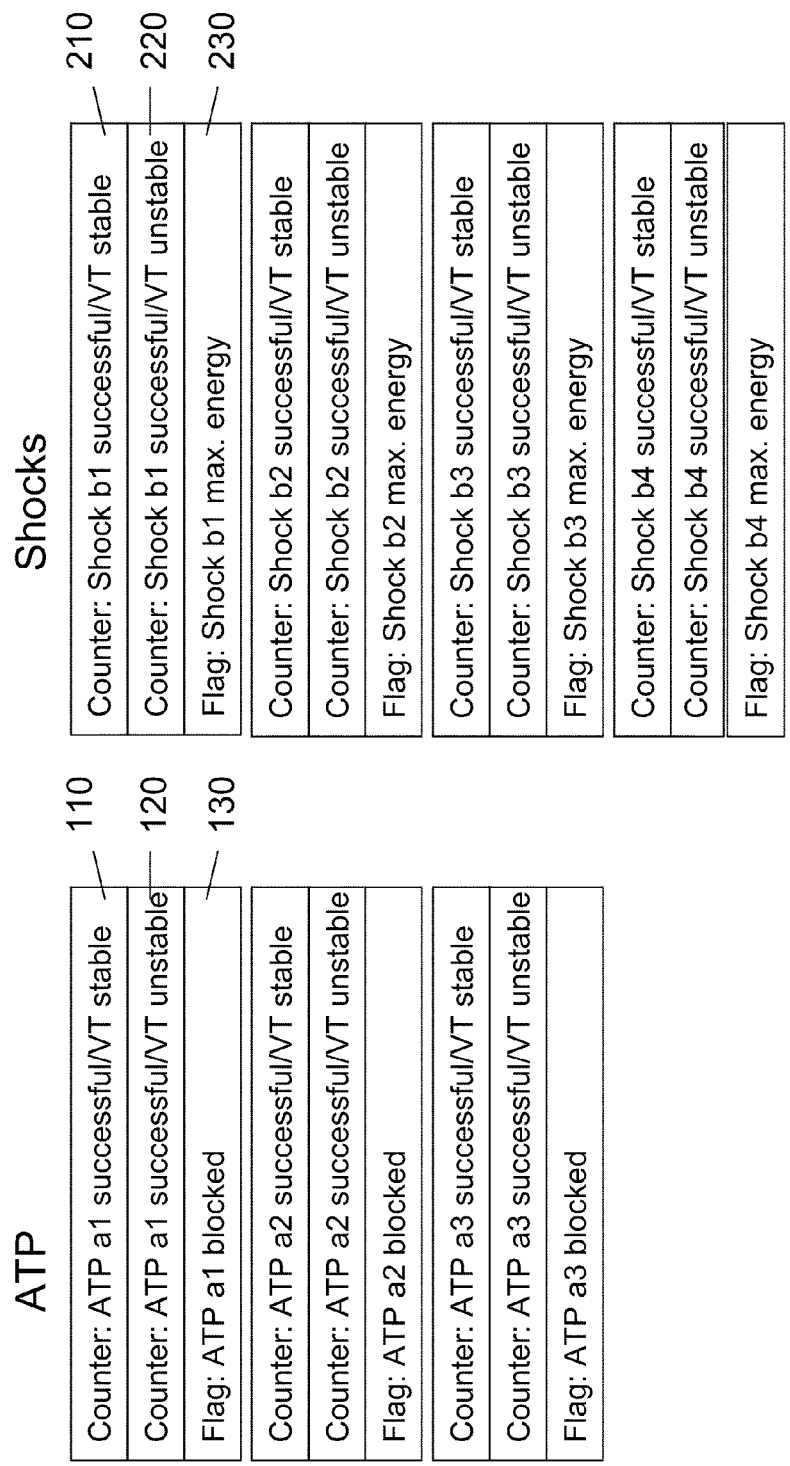
FIG. 5: a memory structure of the therapy success counters.

FIG. 5 shows the structure of the therapy success counters, separated by ATP and shock.

The ATP counter registers the number of successful ATPs in cases of stable VT (110), and the number of successful ATPs in cases of unstable VT (120), for every ATP attempt (a1, a2, a3), and administers a flag (130) that can block this ATP attempt for future therapy (e.g. in case of acceleration of the rhythm as the result of this ATP attempt).

The shock counter registers the number of successful shocks in cases of stable VT (210), and the number of successful shocks in cases of unstable VT (220), for every shock delivered, and administers a flag (230) that indicates whether or not the shock energy of the shock is supposed to be raised to the maximal energy by the electronic implant during the next episode. In this way, an unsuccessful shock will be delivered in the future at an energy less than the maximal energy, thereby increasing patient safety.

Figure 6:
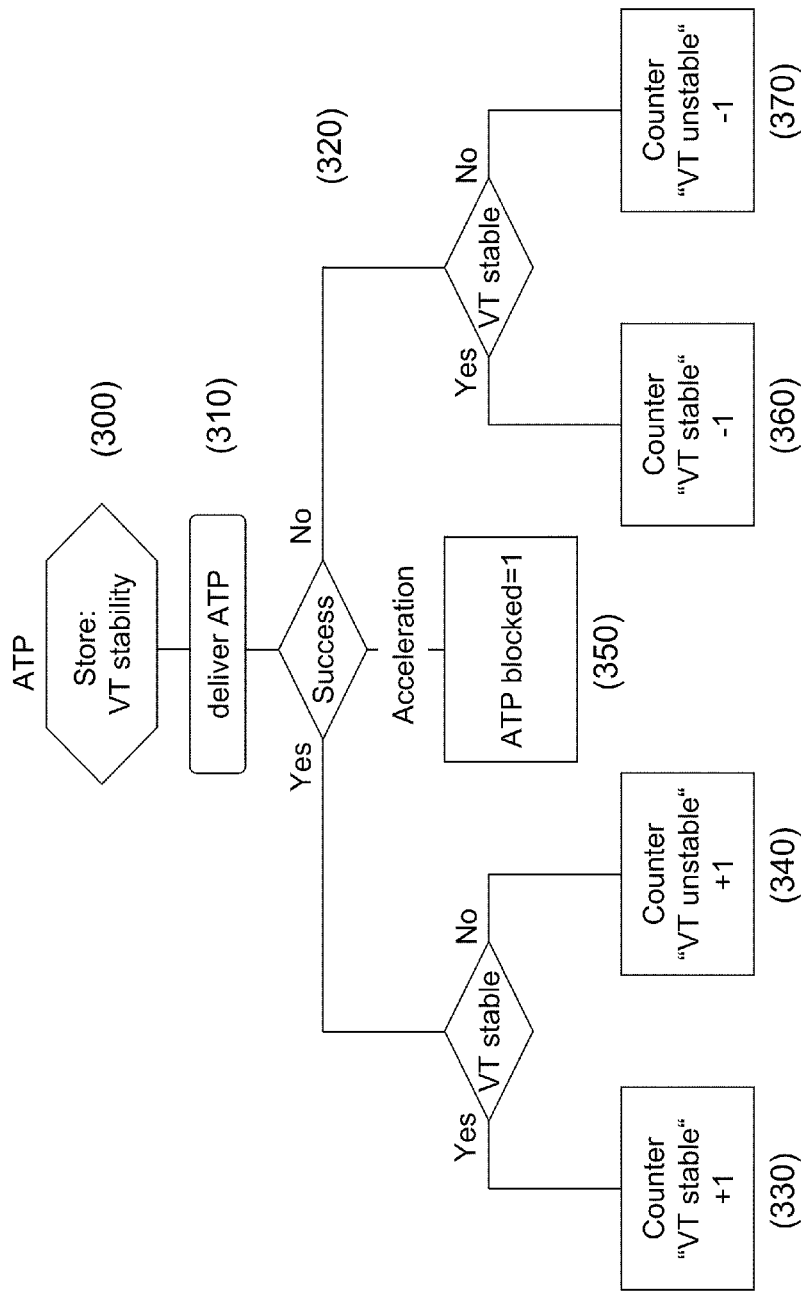
FIG. 6: an illustration of the counting method of the ATP therapy success counter.

FIG. 6 shows the flow chart of therapy success counting for the ATP counter in the VT zones. Immediately before ATP delivery, the data about the stability of the VT to be treated are stored in the implant (300). Subsequently, the ATP is delivered (310), and its therapy success is analyzed by the electronic implant in the subsequent redetection phase (320). If detection of termination takes place after this ATP, it is considered to have been successful (success=yes); if redetection of a VT in the same or a lower VT zone takes place, the ATP is considered to have been unsuccessful (success=no). If redetection in a higher VT zone or in the VF zone takes place after the ATP, the ATP has accelerated the VT (success=acceleration).

If the ATP has been analyzed as having been successful, the ATP success counter for a stable VT (330) or an unstable VT (340) is incremented, depending on the stability state (300) of the VT before ATP delivery.

If the ATP has been analyzed as having been unsuccessful, the ATP success counter for a stable VT (360) or an unstable VT (370) is decremented, depending on the stability state (300) of the VT before ATP delivery. The minimal ATP success counter value is 0.

If, on the other hand, the ATP accelerates the VT into a higher VT zone or into the VF zone, the flag for blocking this ATP is set in the therapy success counter (350). In this connection, the counter readings remain unchanged.

The stability analysis and the acceleration query are eliminated in the VF zone (320).

Figure 7:
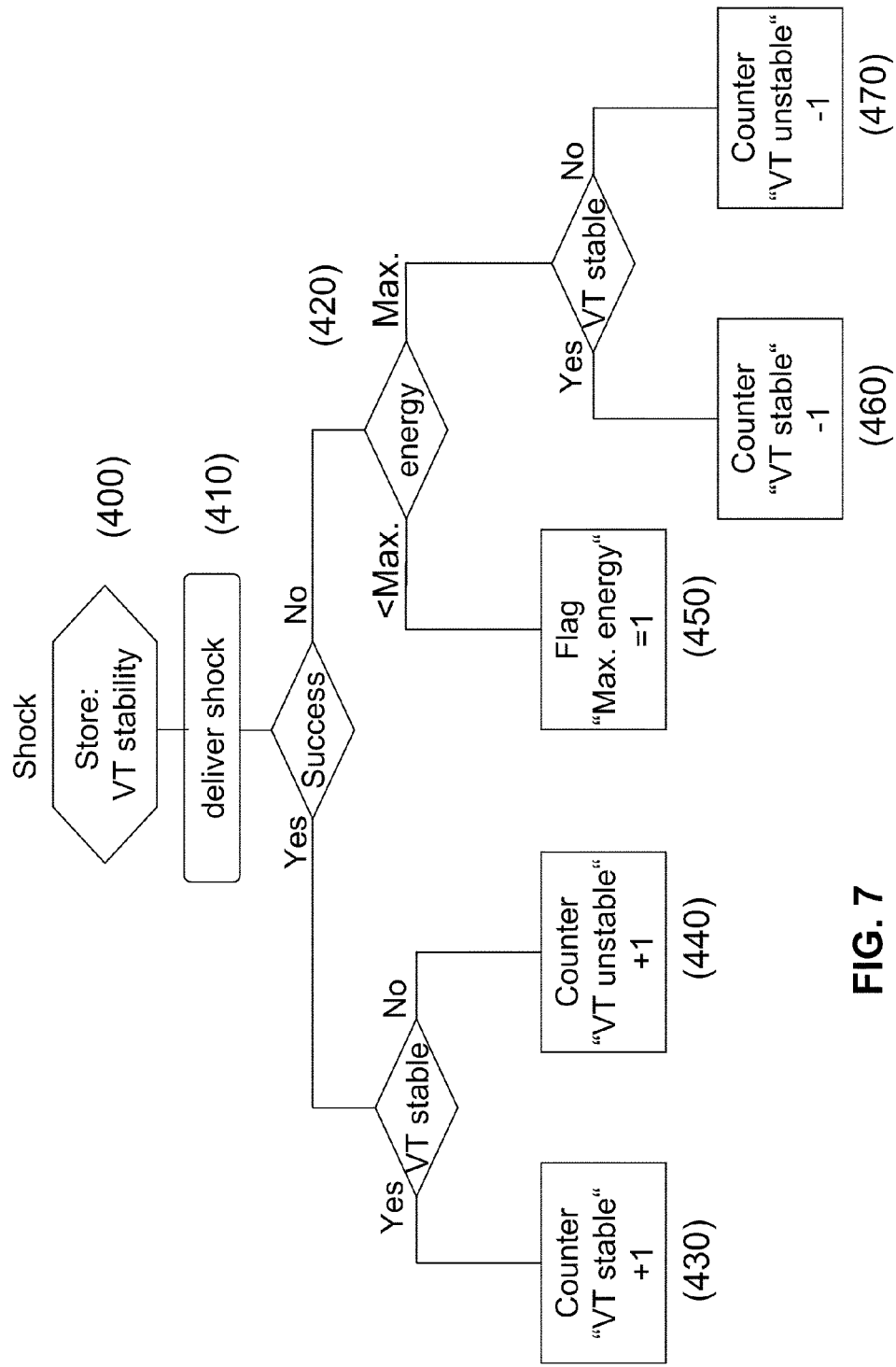
FIG. 7: an illustration of the counting method of the shock therapy success counter.

FIG. 7 shows the flow chart of therapy success counting for the shock counter in the VT zones. Immediately before the start of the charging process for the shock therapy, the data concerning the stability of the VT to be treated are stored in the implant (400). Subsequently, the high-voltage capacitors of the ICD are charged, and after this is completed, the defibrillation shock is delivered (410), and its therapy success is analyzed by the implant during the subsequent redetection phase (420). If detection of termination takes place after the shock (i.e. the tachycardia does not continue to exist after delivery of the shock), it is considered to have been successful (success=yes); if redetection of a VT or of the VF zone takes place (i.e. the tachycardia continues to exist after the shock), the shock is considered to have been unsuccessful (success=no).

If the shock has been assessed as having been successful, the shock success counter for a stable VT (430) or an unstable VT (440) is incremented as a function of the stability state (400) of the VT before charging started.

If the shock has been assessed as having been unsuccessful, a check first takes place to determine whether the energy of this shock is already the maximal energy. If the energy is less than the maximal possible shock energy (energy<max.), the flag for increasing the shock energy to the maximal energy is set in the shock counter (450). The counter reading is not changed.

If the shock energy is already the maximal energy, then the shock success counter for a stable VT (460) or an unstable VT (470) is decremented, depending on the stability state (400) of the VT before the start of charging. In this connection, the minimal counter value is 0.

In the VF zone, the stability analysis is eliminated.

Figure 8:
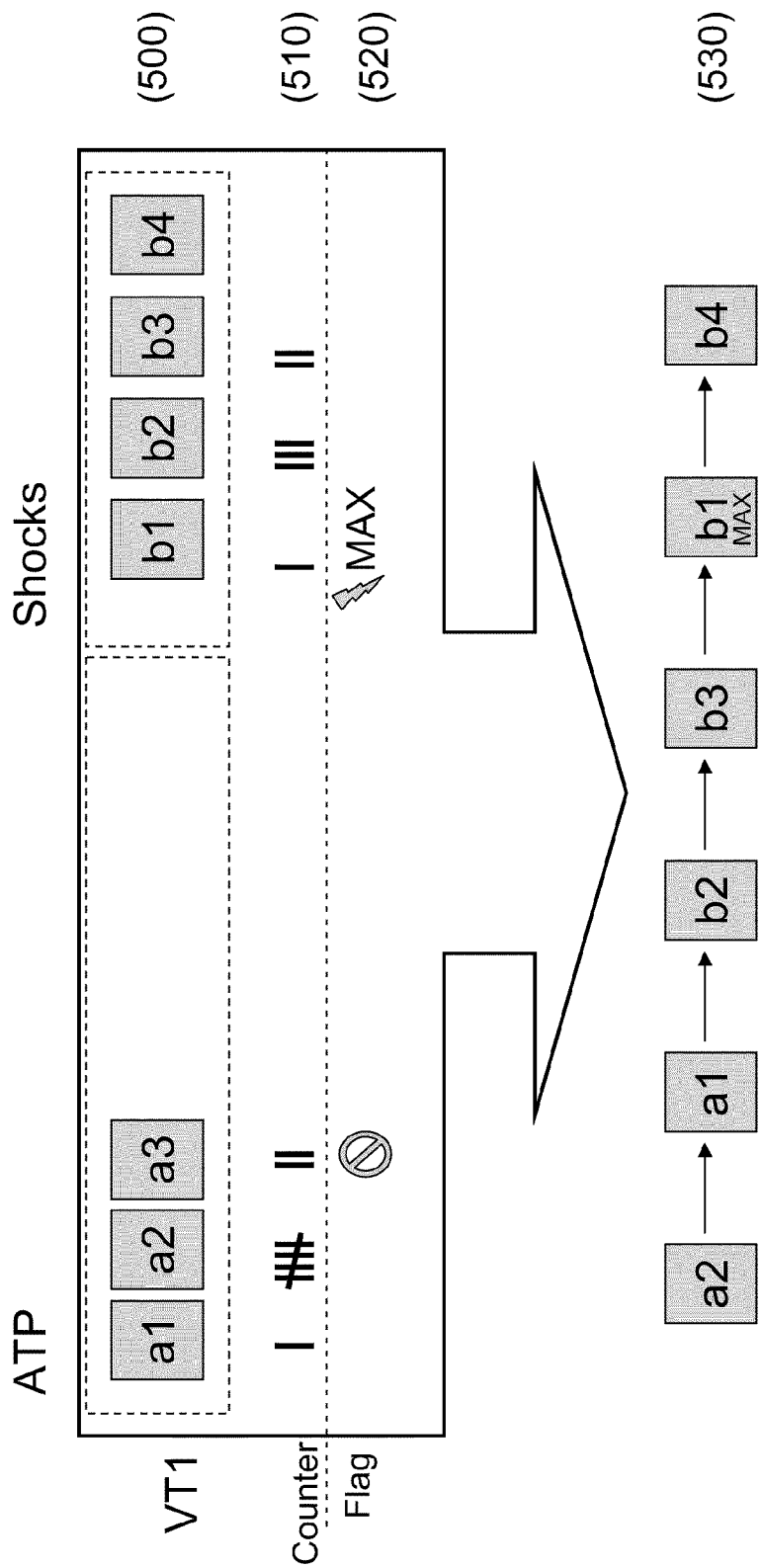
FIG. 8: the adaptation of the therapy sequence in accordance with the therapy success counter.

FIG. 8 illustrates the automatic reorganization of the therapy sequence structure by the therapy device, i.e. by the control unit 54 and the therapy control unit 92.

In the top line, the initially programmed therapy sequence in the VT1 zone is shown (500), consisting of three ATP attempts (a1, a2, a3), and four defibrillation shocks (b1, b2, b3, b4), where in the example shown, the first shock (b1) has a programmed energy less than the maximal energy.

The next line (510) illustrates the therapy successes of the individual therapies, totaled in the past. ATP a1 was successful 1 time; a2 5 times; and a3 2 times. The first shock b1 was effective 1 time, b2 3 times, and b3 2 times.

In the subsequent line, the additional flags are shown (520). Since the ATP a3 led to acceleration of the VT once, the flag (⊘) for blocking this ATP has been set. The first shock b1 was ineffective once, therefore the flag (↯ MAX) for automatically increasing the shock energy has been set.

If a VT occurs in the VT1 zone again, the therapy sequence is worked off in accordance with the lower line (530) owing to the therapy efficiency counters: First, the most successful ATP a2, then ATP a1 are delivered, followed by shock b2, then b3, then b1 (at maximal shock energy), and b4. Because the acceleration flag has been set, ATP a3 is suppressed.

The following features are useful for implementing the foregoing functionality:

An adjustable parameter, here deemed "automatic therapy optimization," has the value range [ON/OFF] (standard value OFF).

If the "automatic therapy optimization" is activated, the "energy," "shock polarity," and "shock shape" parameters are set in a fixed manner for all shocks of a VT or VF zone, as exemplified by FIG. 9. However, the shock energy of the first two shocks remains freely programmable (25 J, 30 J).

For every ATP attempt and every shock in the VT zones, two therapy success counters may be stored in memory: therapy success in the case of stable VT, and therapy success in the case of unstable VT.

The ventricular stability criterion immediately before the detection or redetection is preferably always used for the stability analysis.

A therapy success counter may be stored in memory for every shock in the VF zones.

The therapy success counter may be incremented if the therapy leads to detection of termination of the episode.

The therapy success counter may be decremented if the therapy is followed by redetection in the same or a lower zone, and the counter reading is greater than zero.

The therapy success counter may be deleted (=0) if the therapy is followed by redetection in a higher zone (acceleration).

If an ATP in a VT zone is followed by redetection in the VF zone, then an "ATP blocked" flag may be set in the therapy success counter. In this case, the therapy success counter may remain unchanged.

The therapy success counter remains unchanged if the therapy (DFc) or the episode (programmer) was discontinued.

The therapy success counters are only supposed to be influenced by spontaneous episodes, i.e. not in the case of induced episodes.

The programmer (external programming device) can preferably query the therapy success counters during aftercare, and allow their display to the physician.

The physician can preferably manually reset the therapy success counters using the programmer.

The therapy success counters can preferably be automatically reset by means of the programmer during reprogramming of the therapy sequences, ATP, and shock parameters.

If a shock having an energy less than maximal energy is followed by redetection, then an "energy increase" flag may be set in the therapy success counter. In this case, the therapy success counter reading can remain unchanged.

If Automatic Therapy Optimization is activated, then the order of the therapy sequence can be resorted in accordance with the counter reading of the therapy success counters:

First, the programmed number of ATP attempts is delivered, but not in the programmed order, and rather in the order of decreasing therapy success, separated according to stable and unstable VT at the time of detection/redetection.

If all the ATP attempts have been delivered without success, then the number of programmed shocks is delivered in the order of decreasing therapy success. If the energy increase of a shock is marked, the shock energy of this shock is set to maximal energy.

The invention is not intended to be limited to the preferred versions of the invention described above, but rather is intended to be limited only by the claims set out below. Thus, the invention encompasses all different versions that fall literally or equivalently within the scope of these claims.

What is claimed is:

1. An electrotherapy device for electrical anti-tachycardia therapy of a heart, the device including:
   a. a tachycardia registration unit (90) configured to:
      (1) detect a tachycardia of a ventricle of the heart, and
      (2) record characteristics of the detected tachycardia;
   b. at least one stimulation unit (56, 50) configured to deliver a therapy sequence to the ventricle, each therapy sequence containing a sequence of anti-tachycardia therapies, wherein:
      (1) each anti-tachycardia therapy within the therapy sequence includes the delivery of at least one stimulation/defibrillation pulse to the ventricle, and
      (2) the anti-tachycardia therapies within the therapy sequence differ from one another in one or more therapy characteristics, the therapy characteristics including:
         (a) the intensity of the stimulation/defibrillation pulses,
         (b) the number of the stimulation/defibrillation pulses, and
         (c) the order and timing of the stimulation/defibrillation pulses,
   c. a control unit (54) configured to control the stimulation unit (56, 50) to deliver the therapy sequence to the ventricle after detection of a tachycardia;
   d. a therapy success memory (96);
   e. a therapy success registration unit (90, 92) configured to:
      (1) store data in the therapy success memory (96) characterizing
         (a) the tachycardia, and
         (b) any anti-tachycardia therapy within the therapy sequence resulting in termination of the tachycardia, and
      (2) compile therapy success statistics based on the data stored in the therapy success memory (96),
   wherein the control unit (54, 92) is configured to:
   I. revise the order of the anti-tachycardia therapies within the therapy sequence in dependence on how often each anti-tachycardia therapy within the therapy sequence resulted in termination of a tachycardia in comparison with the other anti-tachycardia therapies of the therapy sequence; and
   II. inhibit subsequent delivery by the stimulation unit (56, 50) of any anti-tachycardia therapy resulting in an accelerating tachycardia, thereby preventing the anti-tachycardia therapy's later usage within the therapy sequence.

2. The electrotherapy device of claim 1 wherein the therapy success statistics include therapy success counter readings stored in the therapy success memory (96).

3. The electrotherapy device of claim 2 in combination with an external programming device separate and spaced from the electrotherapy device, wherein the external programming device is configured to wirelessly access and modify the therapy success counter readings.

4. The electrotherapy device of claim 1 wherein:
   a. each anti-tachycardia therapy within the therapy sequence is assigned a therapy success counter, and
   b. when one of the anti-tachycardia therapies results in termination of the tachycardia, the corresponding therapy success counter is increased.

5. The electrotherapy device of claim 1 wherein the tachycardia registration unit differentiates detected tachycardias into:
   a. stable tachycardias having a stable rhythm, and
   b. unstable tachycardias having an unstable rhythm.

6. The electrotherapy device of claim 5 wherein at least one anti-tachycardia therapy within the therapy sequence is assigned:
   a. a first therapy success counter reading for stable tachycardias, wherein the first therapy success counter reading is increased if the anti-tachycardia therapy resulted in termination of a stable tachycardia, and
   b. a second therapy success counter reading for unstable tachycardias, wherein the second therapy success counter reading is increased if the anti-tachycardia therapy resulted in termination of an unstable tachycardia.

7. The electrotherapy device of claim 1 wherein the tachycardia registration unit is further configured to differentiate detected tachycardias into discrete tachycardia zones as a function of the heart rate.

8. The electrotherapy device of claim 7 wherein at least one anti-tachycardia therapy within the therapy sequence is assigned multiple therapy success counters, each of these therapy success counters corresponding to one of the tachycardia zones.

9. The electrotherapy device of claim 1 wherein:
   a. each anti-tachycardia therapy within the therapy sequence is assigned one or more therapy success counters, and
   b. for any anti-tachycardia therapy resulting in an accelerating tachycardia, the corresponding therapy success counters are decreased.

10. The electrotherapy device of claim 1 in combination with an external programming device separate and spaced from the electrotherapy device, wherein the external programming device is configured to wirelessly receive the therapy success statistics.

11. An electrotherapy device for electrical anti-tachycardia therapy of a heart, the device including:
    a. a tachycardia registration unit (90) configured to detect a tachycardia within a ventricle of the heart;
    b. at least one stimulation unit (56, 50) configured to deliver a therapy sequence to the ventricle after detection of a tachycardia, each therapy sequence containing a sequence of anti-tachycardia therapies, wherein:
       (1) each anti-tachycardia therapy within the therapy sequence includes the delivery of at least one stimulation/defibrillation pulse to the ventricle, and
       (2) the anti-tachycardia therapies within the therapy sequence differ in at least some of their stimulation/defibrillation pulses,
    c. a therapy success memory (96);
    d. a therapy success registration unit (90, 92) configured to store data in the therapy success memory (96) characterizing how often each anti-tachycardia therapy within the therapy sequence resulted in termination of a tachycardia in comparison with the other anti-tachycardia therapies of the therapy sequence, wherein:
I. the order of the anti-tachycardia therapies within the therapy sequence is revised in dependence on how often each anti-tachycardia therapy within the therapy sequence resulted in termination of a tachycardia in comparison with the other anti-tachycardia therapies of the therapy sequence; and
II. any anti-tachycardia therapy resulting in an accelerating tachycardia is removed from the therapy sequence, thereby preventing the anti-tachycardia therapy's later usage within the therapy sequence.

12. The electrotherapy device of claim 11 wherein:
a. each anti-tachycardia therapy within the therapy sequence is assigned one or more therapy success counters, and
b. when one of the anti-tachycardia therapies results in termination of a tachycardia, at least one of the therapy success counters corresponding to the anti-tachycardia therapy is increased.

13. The electrotherapy device of claim 12 wherein when one of the anti-tachycardia therapies fails to result in termination of a tachycardia, at least one of the therapy success counters corresponding to the anti-tachycardia therapy is decreased.

14. The electrotherapy device of claim 11 wherein each anti-tachycardia therapy within the therapy sequence is assigned:
a. a set of stability therapy success counters, the set including:
(1) a stable tachycardia therapy success counter which is increased when the anti-tachycardia therapy results in termination of a tachycardia having a stable rhythm;
(2) an unstable therapy success counter which is increased when the anti-tachycardia therapy results in termination of a tachycardia having an unstable rhythm;
b. a set of zone therapy success counters, each corresponding to a range of heart rates, each zone therapy success counter being increased when the anti-tachycardia therapy results in termination of a tachycardia occurring within the corresponding range of heart rates.

15. The electrotherapy device of claim 14 wherein when one of the anti-tachycardia therapies results in an accelerating tachycardia, at least one of the following occurs:
a. at least one of the therapy success counters corresponding to the anti-tachycardia therapy is decreased;
b. the stimulation unit (56, 50) is blocked from delivery of the anti-tachycardia therapy; and
c. the anti-tachycardia therapy is removed from the therapy sequence.

16. The electrotherapy device of claim 11 in combination with an external programming device separate and spaced from the electrotherapy device, wherein the external programming device is configured to wirelessly receive the data in the therapy success memory (96) characterizing how often each anti-tachycardia therapy within the therapy sequence resulted in termination of a tachycardia in comparison with the other anti-tachycardia therapies of the therapy sequence.

17. An electrotherapy device for electrical anti-tachycardia therapy of a heart, the device including:
a. a tachycardia registration unit (90) detecting a tachycardia of a ventricle of the heart from an intracardiac detection electrode;
b. at least one stimulation unit (56, 50) delivering a therapy sequence to the ventricle via an intracardiac stimulation/defibrillation electrode after detection of a tachycardia, each therapy sequence containing a sequence of anti-tachycardia therapies, wherein:
(1) each anti-tachycardia therapy within the therapy sequence includes the delivery of at least one stimulation/defibrillation pulse to the ventricle,
(2) the anti-tachycardia therapies within the therapy sequence differ in at least some of their stimulation/defibrillation pulses, and
(3) at least some of the anti-tachycardia therapies within the therapy sequence include one or more of:
(a) a set of stability therapy success counters, the set having:
i. a stable tachycardia therapy success counter which is increased when the anti-tachycardia therapy results in termination of a tachycardia having a stable rhythm;
ii. an unstable therapy success counter which is increased when the anti-tachycardia therapy results in termination of a tachycardia having an unstable rhythm;
(b) a set of zone therapy success counters, each zone therapy success counter corresponding to a range of heart rates, each zone therapy success counter being increased when the anti-tachycardia therapy results in termination of a tachycardia occurring within the corresponding range of heart rates,
wherein:
I. the device revises the order of the anti-tachycardia therapies within the therapy sequence in dependence on the therapy success counters, and
II. an anti-tachycardia therapy within the therapy sequence is removed from the therapy sequence if the anti-tachycardia therapy results in acceleration of a tachycardia, thereby preventing the anti-tachycardia therapy's later usage within the therapy sequence.

18. The electrotherapy device of claim 17 wherein each success counter is decreased if the anti-tachycardia therapy does not result in termination of a tachycardia.

* * * * *